United States Patent [19]

Uchida et al.

[11] Patent Number: 4,910,217

[45] Date of Patent: Mar. 20, 1990

[54] CURING AGENT FOR FAT NECROSIS AND METHOD FOR CURING SAID DISEASE

[75] Inventors: Matazaemon Uchida, Kawachinagano; Masakazu Shibayama, Takatsuki; Isao Nishino, Kunitachi; Harutaka Kimura, Tokyo, all of Japan

[73] Assignee: Nihon Nohyaku Co., Ltd., Tokyo, Japan

[21] Appl. No.: 946,044

[22] Filed: Dec. 24, 1986

[30] Foreign Application Priority Data

Dec. 28, 1985 [JP] Japan ..................... 60-293652

[51] Int. Cl.$^4$ .................... A61K 31/38; A61K 31/385
[52] U.S. Cl. ..................... 514/430; 514/440; 514/441
[58] Field of Search .............. 514/430, 440, 441

[56] References Cited

U.S. PATENT DOCUMENTS

| 4,022,907 | 5/1977 | Taninaka et al. | 424/277 |
|---|---|---|---|
| 4,080,466 | 3/1978 | Taninaka et al. | 424/277 |
| 4,080,467 | 3/1978 | Taninaka et al. | 424/277 |
| 4,118,506 | 10/1978 | Taninaka et al. | 424/277 |
| 4,564,627 | 1/1986 | Hokazono et al. | 514/530 |

FOREIGN PATENT DOCUMENTS

| 6234126 | 8/1972 | Japan . |
|---|---|---|
| 49-17566 | 5/1974 | Japan . |
| 51-34883 | 9/1976 | Japan . |
| 54-7852 | 4/1979 | Japan . |
| 58-185581 | 10/1983 | Japan . |

*Primary Examiner*—Frederick E. Waddell
*Attorney, Agent, or Firm*—Cushman, Darby & Cushman

[57] ABSTRACT

A curing agent for fat necrosis which contains a dithia derivative represented by the general formula

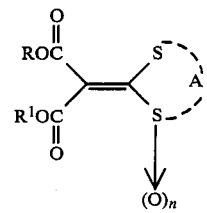

wherein R and R$^1$ may be either the same or different and denote a lower alkyl group; n denotes an integer of 0, 1 or 2; and A denotes —CH$_2$—,

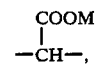

M being H or a salt-forming rest, —CH=CH—, —CH$_2$CH$_2$—, or

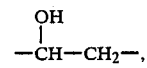

and a method for curing said disease using the said curing agent.

3 Claims, 2 Drawing Sheets

CURING AGENT FOR FAT NECROSIS AND METHOD FOR CURING SAID DISEASE

FIELD OF THE INVENTION

This invention relates to a curing agent for fat necrosis which contains a dithia derivative represented by the general formula (I)

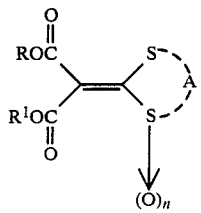

wherein R and $R^1$ may be either the same or different and denote a lower alkyl group; n denotes an integer of 0, 1 or 2; and A denotes $-CH_2-$;

M being H or a salt-forming rest, $-CH=CH-$, $-CH_2-CH_2-$ or

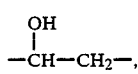

and a method for curing the said disease which uses the said curing agent.

RELATED ARTS

Fat necrosis of domestic animals has hitherto frequently occurred particularly in domestic cattle such as breeding cattle and beef cattle, and very few cases have been reported for pigs and chickens.

The disease of cattle presently called fat necrosis has been known from old times in Japan as well as in foreign countries. It is a disease in which fatty tissue mainly in the abdominal cavity forms a mass, causing trouble to a living body.

The tissue is found to develop mainly in the kidney, the colon, the circumference of the rectum, and the circumference of the kidney. There are two types of the mass. In one type, the mass forms a hard lump ranging in size from a small finger to a volleyball. In the other type, the mass does not form a hard lump but appears in the form of yellowish white leisons of a poppy seed size not only in the intestinal cavity but nearly over the whole body including the thoracic cavity and subcutaneous and intermuscular sites. The former type is more commonly observed.

The symptoms of this disease include extinction of appetite, diarrhea, bloody excrement, excretion of hard feces, colic pain, and leanness. Cattle suffering the disease will fall into a digestive trouble or a breeding disturbance and, in many cses, die or become useless.

In Japan, the onset of fat necrosis of cattle was first reported in 1966 in Nagano Prefecture, and since then has frequently occurred mainly in breeding Japanese Cattle. However, the definite cause of the disease is yet unknown. Since no specific medicine is known for fat necrosis, there have been hitherto conducted, as a tentative measure, confirmation of the disease by rectum inspection and early-stage slaughter of cattle suffering the disease, and cure or prevention by means of adlay or coix seed (an adlay constituent) preparations. However, these measures are not always satisfactory in their efficacy. Adlay is cultivated in Japan as a herb medicine in warm places and marshy ground in the Kanto district and westward, but not as a food crop. Worldwide also, it is produced only in a limited quantity.

For reasons mentioned above, feeding of adlay or the like for the cure or prevention of fat necrosis is not smoothly conducted at present.

SUMMARY OF THE INVENTION

An object of this invention is to provide a curing agent for fat necrosis. Another object of this invention is to provide a method for curing the said disease which uses the said curing agent.

BRIEF DESCRIPTION OF THE DRAWING

FIG. 1 shows the change of lipid components and FIG. 2 the change of the other components.

DETAILED DESCRIPTION OF THE INVENTION

Figure 1:
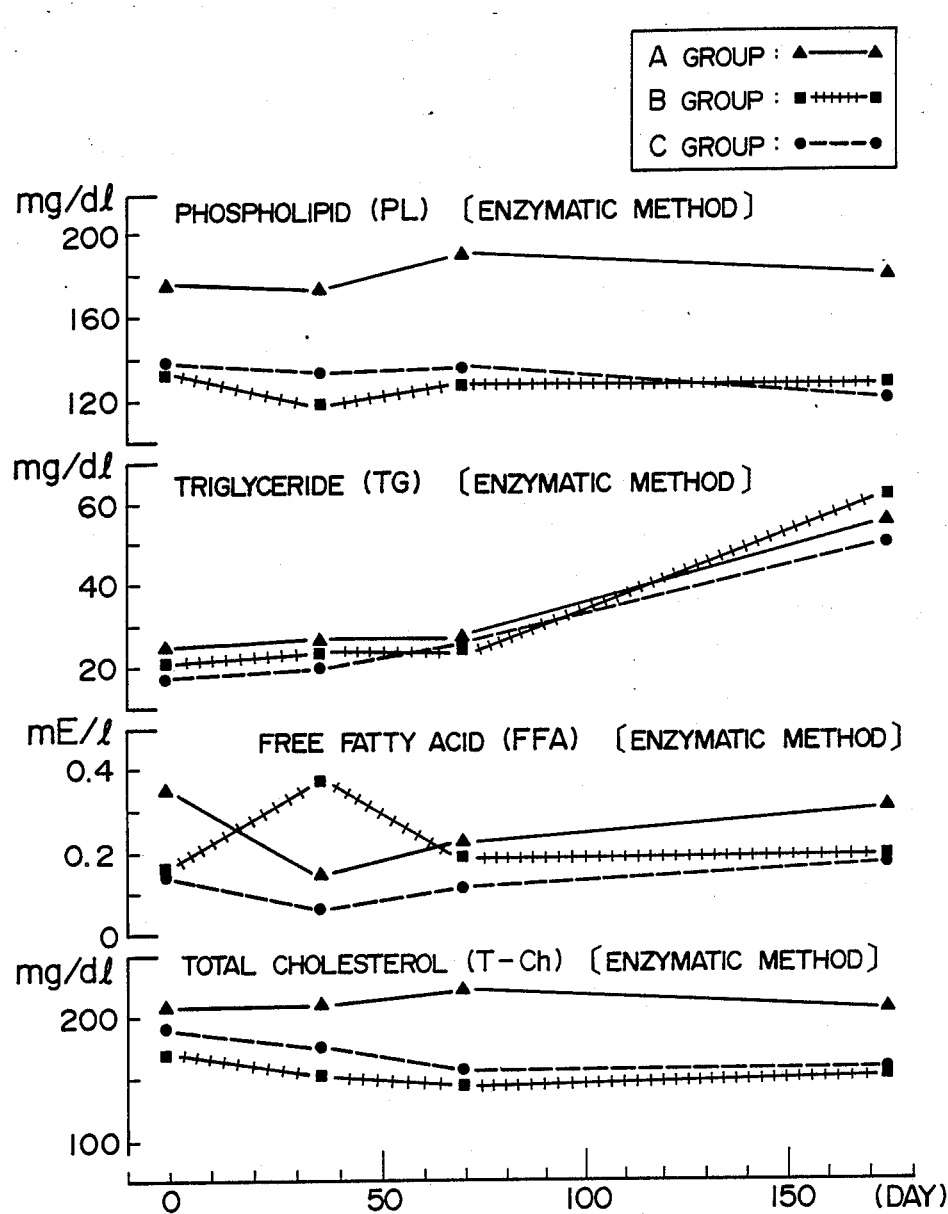
FIGS. 1 and 2 are graphs showing the change of serum components with the lapse of time in Cure Test I.

In view of the present circumstances mentioned above, the present inventors have made extensive studies to find an effective curing agent or a curing method for fat necrosis which can take the place of adlay, and paid their attention to the compound of the above-mentioned general formula. This compound is already known as a curative for liver disorders of men and animals from U.S. Pat. Nos. 4,080,467, 4,080,466, 4,022,907, and 4,118,506, as a germicide for agricultural and horticultural use from Japanese Patent Application Kokoku (Post-Exam. Publn.) Nos. 34,883/76 and 34,126/72, and as a livestock feed composition from U.S. Pat. No. 4,564,627. The curing agent for liver disorders mentioned above shows pharmacologically (1) a liver protein synthesis promoting action and (2) a liver fibrosis suppressing action, and is used as a preventing or curing agent for various liver disorders including adiposis hepatica, hepatocirrhosis, toxic hepatic disorder, and congestion of blood. It is believed that its effect lies in transferring the fat present in the liver to other tissues thereby to reduce the amount of fat in the liver. As to the use as the livestock feed composition, its object is to reduce the fat present in the abdominal cavity thereby to prevent the lowering of meat utilization efficiency (carcass efficiency) which would be caused by the cattle growing corpulent as the result of accumulation of excess fat in the visceral cavity. Thus, it has been believed that such fat present in excess in the liver or the abdominal cavity is utterly different from the morbidly denatured fat formed in the mass of fat necrosis described below, and hence reducing the fat accumulated in excess under such normal conditions has no relation with removing the morbidly denatured fat of mass thereby to cure morbid animals and recover their health. Accordingly, it was utterly unexpected that the compound having the above-mentioned general formula of this invention should be effective for the present disease. Thus, in fat necrosis, according to microscopic inspection of the cells thereof, lively historytic cells are present on the outside thereof, these cells enclose the fat cells of the inside, the fat cells have been necrosed nearly completely and the central portion thereof give an indistinct image on dyeing, and saturated solid fat is observed inside the fat cells. According to an example of analysis of the fat, the ratio of unsaturated fatty acid to saturated fatty acid is 0.691 on the average, which shows, as compared with the value of 0.987 of the fat in a normal part, that the proportion of saturated fatty acid is larger in the necrosed part.

Accordingly, in view of such a state of extinction of mass tissue in fat necrosis and the marked difference of its fat composition from normal ones, it was utterly unanticipated that the compound of the present invention should act effectively on the disease.

In the meantime, the present inventors have made comparative tests between curing agents using the compound employed in this invention in combination with adlay, plant sterol, or vitamin E, most commonly employed hitherto, and those using the compound of this invention alone, with the object of improving the efficacy of prior art drugs. The tests were conducted in an attempt to develop a curing agent that is more effective for the mass by combined use of the two types of drugs, and the compound of this invention itself was used as an adjuvant and was not expected to play the principal role in curing the mass. Unexpectedly, it has been found that the compound of this invention is in itself markedly effective in improving the condition of mass and/or curing the mass when used alone. Thus, it has been found that the compound of this invention has a marked effect in curing the denatured fat of the lesion of mass.

Specific example of the various compounds usable in this invention are shown in Table 1.

Some embodiments of this invention will be described below in comparison with examples of cure by means of the prior art.

EXAMPLE

Fat Necrosis Cure Test

1. Material and method
(1) Cure Test I:

Cure Test I comprised treating test animals by oral administration mainly of soy sterol, which is a by-product of soybean oil production and contains 20% of plant sterol and 4% of vitamin E, and partly of a combination thereof with adlay.

The animals tested were nine head of cattle at the age of 3 to 8 years suffering from fat necrosis (body weight: 400 to 520 kg) and were divided into three groups of A, B and C each consisting of 3 animals.

To the A group were administered 50 g of soy sterol and 30 g of pulverized adlay, to the B group 150 g of soy sterol, and to the C group 200 g of soy sterol, respectively per day per animal continuously for 175 days from Sept. 9, 1982 to Feb. 21, 1983.

Figure 2:
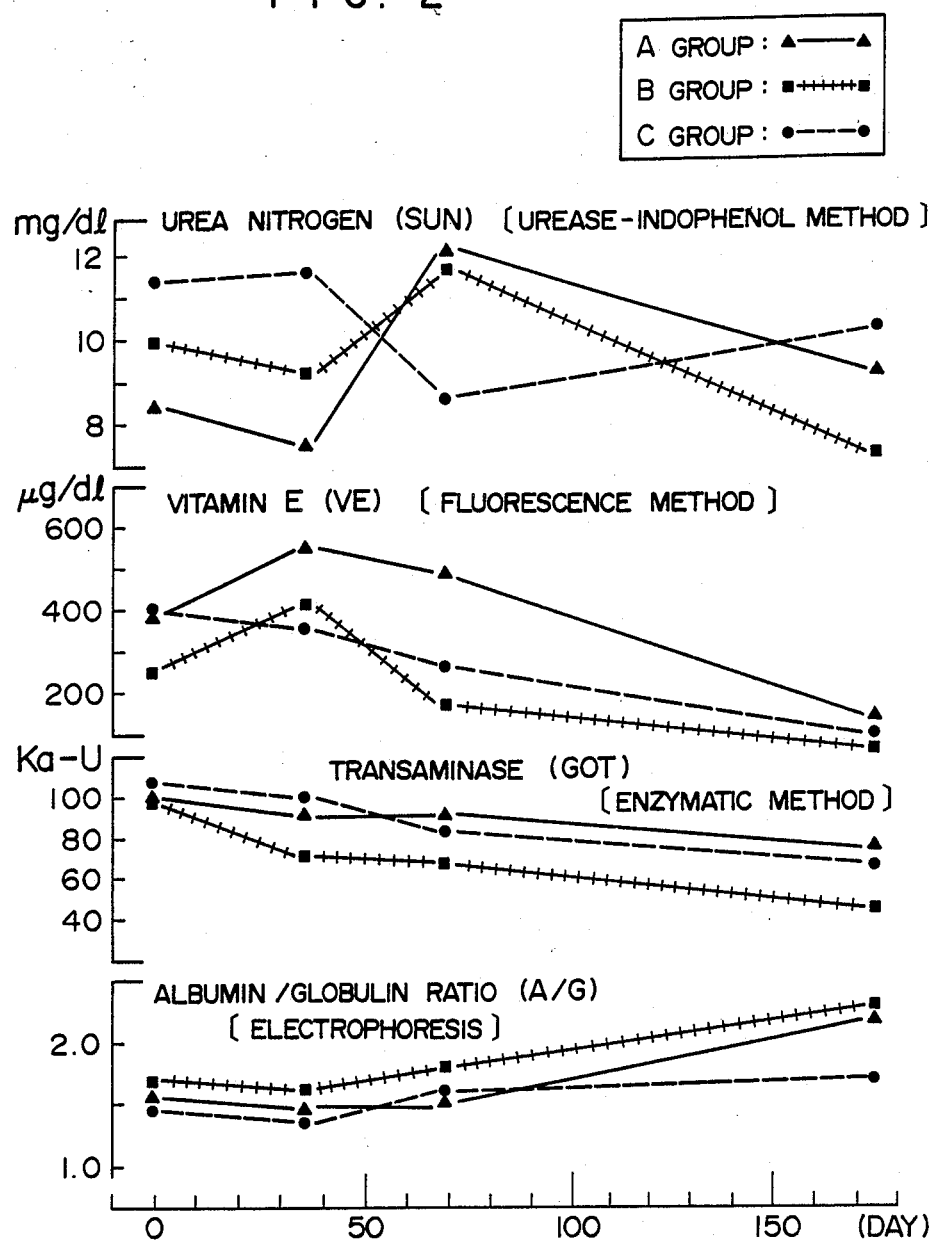

During the period, rectum inspection for confirmation of necrosis lump was conducted 6 times (before administration and on the 37th, 70th, 97th, 144th and 174th day), and also phospholipid (PL), triglyceride (TG) etc. in serum were determined. The results of determination for respective test items are shown in FIGS. 1 and 2.

(2) Cure Test II:

Cure Test II was conducted by treating 4 head of cattle suffering from fat necrosis (body weight: 450 to 530 kg) by oral administration, in the same manner as in

TABLE 1

| Compound No. | A | n | R | $R^1$ | m.p. or b.p. | $LD_{50}$, mouse |
|---|---|---|---|---|---|---|
| 1 | $-CH_2-$ | 0 | $i-C_3H_7$ | $i-C_3H_7$ | m.p 104–105° C. | >5,000 mg/kg |
| 2 | $-CH_2-$ | 0 | $C_2H_5$ | $i-C_3H_7$ | m.p 37–39° C. | >5,000 mg/kg |
| 3 | $\begin{array}{c}COOH\\|\\-CH-\end{array}$ | 0 | $i-C_3H_7$ | $i-C_3H_7$ | m.p 170–171° C. | >5,000 mg/kg |
| 4 | $-CH=CH-$ | 0 | $i-C_3H_7$ | $i-C_3H_7$ | m.p 55–57° C. | 3,120 mg/kg |
| 5 | $-CH=CH-$ | 0 | $C_2H_5$ | $C_2H_5$ | m.p 113° C. | 4,900 mg/kg |
| 6 | $-CH_2-CH_2-$ | 0 | $i-C_3H_7$ | $i-C_3H_7$ | m.p 54.5–55° C. | 1,350 mg/kg |
| 7 | $-CH_2-CH_2-$ | 1 | $i-C_3H_7$ | $i-C_3H_7$ | m.p 78–83° C. | >6,000 mg/kg |
| 8 | $\begin{array}{c}OH\\|\\-CH_2-CH-\end{array}$ | 0 | $i-C_3H_7$ | $i-C_3H_7$ | m.p 73–74° C. | >6,590 mg/kg |

The compounds shown in Table 1 have very low toxicity to warm-blooded animals, and are classified as substances of low toxicity in regulations for the control of deleterious or poisonous substances in various nations. Accordingly, they can usually be used, in oral administration, in the range of 0.01 to 100 mg per 1 kg of body weight. When mixed into livestock feed etc., they can be used in the range of concentration of 10 to 2000 ppm in the feed. For the purpose of curing the present disease in domestic cattle, the dosage is preferably increased or decreased in accordance with the body weight, centering around 25 g per day per animal.

The curing agent of this invention may be administered in any desired form including tablets, injections, particles, granules, and powders. Although oral administration is generally convenient, this invention is not limited thereto.

Cure Test I, mainly of the compound No. 6 of Table 1, namely isoprothiolane.

Cattle No. 1 was given for 91 days starting from Oct. 29, 1983, and Cattle Nos. 2, 3 and 4 were given for 48 days starting from June 21, 1984, respectively 25 g of isoprothiolane per day per animal, Cattle No. 4 alone being additionally given 100 g of adlay.

The test items were approximately the same as in Cure Test I. Cattle No. 1 was subjected to 8 times in total (before administration and on the 8th, 12nd, 19th, 26th, 57th, 72nd, and 91st day) of blood sample collection and 6 times (before administration and on the 18th, 48th, 57th, 72nd, and 91st day) of rectum inspection. Cattle Nos. 2, 3 and 4 were subjected to 3 times (before administration and on the 18th and 48th day) of the inspection.

2. Result (1) Changes in necrosis lump:

Tables 2 and 3 give schematical representation of the state of necrosis lumps before administration and those in the course of curing treatment, showing respectively the size of necrosis lumps and the development of wrinkles and constrictions.

In Test I, in which the size of necrosis lumps of tested cattle before administration varied widely from a diameter of 3 cm to a case wherein the color was strictured and the necrosis lump could not be confirmed, the reduction of size of necrosis lumps could be observed from the 37th day after administration in an early case, and begun in 70 days after administration even in a late case. In mild cases wherein the necrosis lump was small, the reduction of size proceeded smoothly, sometimes leading to complete cure and stoppage of administration. In serious cases, however, the necrosis lumps reduced their size to a certain extent but not further thereafter. Further, though depending on the conditions of the necrosis lumps of treated cattle, groups B and C, wherein the amount of soy sterol administered was larger, showed a tendency to reduce the size of necrosis lumps faster, among groups A, B and C.

In Test II, the necrosis lumps began to reduce their size approximately after 18 days from administration in each of fat necrosis cattle. In cattle No. 1, the necrosis lump became almost unperceivable by touch in 91 days. Also in 3 other head of cattle, the necrosis lumps reduced their size respectively.

Thus, the above-mentioned compound No. 6 showed a curative effect of faster size reduction of necrosis lumps after initiation of administration as compared with the control tests of groups A, B and C. Tables 2 and 3 are shown below.

What is claimed is:

1. A method for curing fat necrosis which comprises administering to diseased cattle a curing agent for fat necrosis which contains an effective amount of a dithia derivative represented by the general formula

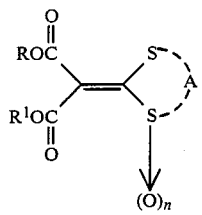

wherein R and $R^1$ may be either the same or different and denote a lower alkyl group; n denotes an integer of 0, 1 or 2; and A denotes $—CH_2—$, $$\begin{matrix} \text{COOM} \\ | \\ —CH— \end{matrix},$$

M being H or a salt-forming rest, $—CH=CH—$, $—CH_2CH_2—$, or $$\begin{matrix} \text{OH} \\ | \\ —CH—CH_2— \end{matrix}.$$

2. A method for curing fat necrosis according to claim 1 wherein a curing agent for fat necrosis which contains 10 to 2,000 ppm of the compound represented by the said general formula is administered.

3. A method for curing fat necrosis according to claim 1 or 2 wherein the compound represented by the said general formula is diisopropyl 1,3-dithiolan-2-ylidenemalonate or diisoproypl 1,3-dithiol-2-ylidenemalonate.

TABLE 2

| Test Group | Animal No. | Site and size of necrosis before administration (unit: cm) | Change of necrosis part during cure (day) *1 | | | | | |
|---|---|---|---|---|---|---|---|---|
| | | | 0 | 37 | 70 | 97 | 144 | 174 |
| A | 1 | Upper part of rectum θ6-7 | | | | | | complete cure |
| | 2 | Upper part of rectum θ8, θ18 | | | | | | |
| | 3 | Upper part of uterus θ25 | NT*2 | | | | | |
| | 4 | Lower part of right kidney θ20 | | | Complete cure | | stoppage of administration | |
| B | 5 | Inner part of rectum θ3 | | | | | | |
| | 6 | Upper part of rectum θ15 | | | | | | |
| | 7 | Circumference of left kidney θ40 | | | | | | |
| C | 8 | Strictured rectum | | | | | | |
| | 9 | Slightly strictured recturm | | | | | | |

*1 State of necrosis lump  Diameter cm:  >5    5-10  11-20  21-30  >30  Strictured rectum Wrinkle development: 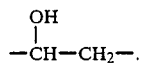    Constriction development: ⦵

*2 NT = Not tested

TABLE 3

| Animal No. | Site and size of necrosis before administration (unit: cm) | Change of necrosis part during cure (day)*3 | | | | | |
|---|---|---|---|---|---|---|---|
| | | 0 | 18 | 48 | 57 | 72 | 91 |
| 1 | Slightly strictured rectum | | | | | | |
| 2 | Lower part of rectum θ8 × 3 × 3 Lower left part of θ3 × 3 × 3 rectum | | | | Test finished | | |
| 3 | Lower part of rectum θ8 × 7 × 2 | | | | | | |
| 4 | Lower part of rectum θ15 × 5 × 5 θ3 × 3 × 3 | | | | | | |

*3 See the footnote for Table 2.

* * * * *